(12) United States Patent
Peters et al.

(10) Patent No.: US 9,042,979 B2
(45) Date of Patent: May 26, 2015

(54) COMBINATION HEART ASSIST SYSTEMS, METHODS, AND DEVICES

(71) Applicant: Sunshine Heart Company PTY LTD, NSW (AU)

(72) Inventors: William S. Peters, Auckland (NZ); Rodney G. Parkin, Crows Nest (AU); David Rosa, Eden Prairie, MN (US); Daniel M. Lafontaine, Plymouth, MN (US); William T. Abraham, Dublin, OH (US); Benjamin Sun, Eden Prairie, MN (US)

(73) Assignee: Sunshine Heart Company Pty Limited, Clontarf, NSW (AU)

( * ) Notice: Subject to any disclaimer, the term of this patent is extended or adjusted under 35 U.S.C. 154(b) by 0 days.

(21) Appl. No.: 14/167,143

(22) Filed: Jan. 29, 2014

(65) Prior Publication Data

US 2014/0148639 A1    May 29, 2014

Related U.S. Application Data

(62) Division of application No. 13/078,666, filed on Apr. 1, 2011.

(60) Provisional application No. 61/320,549, filed on Apr. 2, 2010.

(51) Int. Cl.
*A61N 1/37*    (2006.01)
*A61M 1/10*    (2006.01)
(Continued)

(52) U.S. Cl.
CPC .............. *A61N 1/3702* (2013.01); *A61M 1/006* (2014.02); *A61M 1/1068* (2013.01); *A61M 1/12* (2013.01);
(Continued)

(58) Field of Classification Search
CPC ............ A61N 1/3931; A61N 1/36514; A61N 1/3702; A61N 1/37; A61M 1/107; A61M 1/12; A61M 1/006
USPC ...................... 607/3; 623/3.1, 3.28
See application file for complete search history.

(56) References Cited

U.S. PATENT DOCUMENTS

| 283,660 | A | 8/1883 | Reed |
| 929,571 | A | 7/1909 | Dubied |

(Continued)

FOREIGN PATENT DOCUMENTS

| AU | 2003277983 | 6/2008 |
| DE | 1541311 | 9/1969 |

(Continued)

OTHER PUBLICATIONS

Seymour Furman et al., "Cardiac Support by Periaortic Diastolic Augmentation", New York Journal of Medicine, Aug. 1, 1970, pp. 1964-1969.

(Continued)

*Primary Examiner* — Christopher D Koharski
*Assistant Examiner* — Jeremiah Kimball
(74) *Attorney, Agent, or Firm* — Davis, Brown, Koehn, Shors & Roberts, P.C.

(57) ABSTRACT

The various embodiments disclosed herein relate to combination heart assist systems, methods, and devices that include both an electrical therapy device and a mechanical heart assist device. Various operational modes can be implemented using these embodiments, including a synchronized pacing mode, an internal CPR mode, and an internal workout mode.

23 Claims, 4 Drawing Sheets

(51) Int. Cl.
*A61M 1/12* (2006.01)
*A61N 1/365* (2006.01)
*A61N 1/39* (2006.01)
*A61B 5/00* (2006.01)
*A61B 5/02* (2006.01)
*A61B 5/021* (2006.01)
*A61B 5/026* (2006.01)
*A61B 5/0402* (2006.01)
*A61B 7/02* (2006.01)
*A61B 7/04* (2006.01)
*A61N 1/362* (2006.01)
*A61M 1/00* (2006.01)

(52) U.S. Cl.
CPC ......... *A61N 1/36514* (2013.01); *A61N 1/36521* (2013.01); *A61N 1/36542* (2013.01); *A61N 1/3962* (2013.01); *A61M 1/122* (2014.02); *A61B 5/0084* (2013.01); *A61B 5/02028* (2013.01); *A61B 5/021* (2013.01); *A61B 5/026* (2013.01); *A61B 5/0402* (2013.01); *A61B 5/4836* (2013.01); *A61B 5/686* (2013.01); *A61B 7/023* (2013.01); *A61B 7/04* (2013.01); *A61M 1/1072* (2013.01); *A61M 1/1086* (2013.01); *A61N 1/3627* (2013.01)

(56) References Cited

U.S. PATENT DOCUMENTS

| | | |
|---|---|---|
| 1,576,397 A | 7/1925 | Yanagi |
| 1,719,316 A | 7/1929 | Appleton |
| 3,467,077 A | 9/1969 | Cohen |
| 3,552,383 A | 1/1971 | Krueger et al. |
| 3,597,766 A | 8/1971 | Buck |
| 4,014,318 A | 3/1977 | Dockum et al. |
| 4,051,840 A | 10/1977 | Kantrowitz et al. |
| 4,176,411 A | 12/1979 | Runge |
| 4,195,623 A | 4/1980 | Zeff et al. |
| 4,236,482 A | 12/1980 | Gingerich et al. |
| 4,256,094 A | 3/1981 | Kapp |
| 4,277,706 A | 7/1981 | Issacson |
| 4,304,225 A | 12/1981 | Freeman |
| 4,454,891 A | 6/1984 | Dreibelbis et al. |
| 4,457,673 A | 7/1984 | Conley et al. |
| 4,459,977 A | 7/1984 | Pizon et al. |
| 4,515,587 A | 5/1985 | Schiff |
| 4,583,523 A | 4/1986 | Kleinke et al. |
| 4,594,731 A | 6/1986 | Lewkowicz |
| 4,630,597 A | 12/1986 | Kantrowitz et al. |
| 4,676,482 A | 6/1987 | Reece et al. |
| 4,697,574 A | 10/1987 | Karcher et al. |
| 4,737,083 A | 4/1988 | Meyer |
| 4,763,646 A | 8/1988 | Lekholm |
| 4,771,765 A | 9/1988 | Choy et al. |
| 4,809,676 A | 3/1989 | Freeman |
| 4,813,952 A | 3/1989 | Khalafalla |
| 4,822,357 A | 4/1989 | Forster et al. |
| 4,881,939 A | 11/1989 | Newman |
| 4,925,443 A | 5/1990 | Heilman et al. |
| 4,957,477 A | 9/1990 | Lundback |
| 4,979,936 A | 12/1990 | Stephenson et al. |
| 5,089,017 A | 2/1992 | Young et al. |
| 5,169,378 A | 12/1992 | Figuera |
| 5,197,980 A | 3/1993 | Gorahkov et al. |
| 5,205,810 A | 4/1993 | Guiraudon et al. |
| 5,222,980 A | 6/1993 | Gealow |
| 5,267,940 A | 12/1993 | Moulder |
| 5,273,518 A | 12/1993 | Lee et al. |
| 5,290,249 A | 3/1994 | Foster et al. |
| 5,300,111 A | 4/1994 | Panton et al. |
| 5,337,752 A | 8/1994 | Reeves |
| 5,344,385 A | 9/1994 | Buck et al. |
| 5,346,458 A | 9/1994 | Affeld |
| 5,360,445 A | 11/1994 | Goldowsky |
| 5,372,573 A | 12/1994 | Habib |
| 5,383,915 A | 1/1995 | Adams |
| 5,429,584 A | 7/1995 | Chiu |
| 5,447,523 A | 9/1995 | Schaldach |
| 5,453,076 A | 9/1995 | Kiyota et al. |
| 5,511,551 A | 4/1996 | Sano et al. |
| 5,554,177 A | 9/1996 | Kieval et al. |
| 5,569,156 A | 10/1996 | Mussivand |
| 5,593,414 A | 1/1997 | Shipp et al. |
| 5,607,378 A | 3/1997 | Winston |
| 5,647,380 A | 7/1997 | Campbell et al. |
| 5,722,930 A | 3/1998 | Larson, Jr. et al. |
| 5,792,195 A | 8/1998 | Carlson et al. |
| 5,814,012 A | 9/1998 | Fleenor et al. |
| 5,820,542 A | 10/1998 | Dobak, III et al. |
| 5,827,171 A | 10/1998 | Dobak, III et al. |
| 5,833,655 A | 11/1998 | Freed et al. |
| 5,843,170 A | 12/1998 | Ahn |
| 5,876,434 A | 3/1999 | Flomenblit |
| 5,975,140 A | 11/1999 | Lin |
| 5,980,448 A | 11/1999 | Heilman et al. |
| 6,030,336 A | 2/2000 | Franchi |
| 6,030,366 A | 2/2000 | Mitchell |
| 6,045,496 A | 4/2000 | Pacella et al. |
| 6,066,085 A | 5/2000 | Heilman et al. |
| 6,132,363 A | 10/2000 | Freed et al. |
| 6,132,636 A | 10/2000 | Singh et al. |
| 6,146,325 A | 11/2000 | Lewis et al. |
| 6,210,318 B1 | 4/2001 | Lederman |
| 6,210,319 B1 | 4/2001 | Williams et al. |
| 6,226,843 B1 | 5/2001 | Crainich |
| 6,251,061 B1 | 6/2001 | Hastings et al. |
| 6,406,422 B1 | 6/2002 | Landesberg |
| 6,432,039 B1 | 8/2002 | Wardle |
| 6,471,633 B1 | 10/2002 | Freed |
| 6,553,263 B1 | 4/2003 | Meadows et al. |
| 6,572,534 B1 | 6/2003 | Milbocker et al. |
| 6,585,635 B1 | 7/2003 | Aldrich |
| 6,616,596 B1 | 9/2003 | Milbocker |
| 6,626,821 B1 | 9/2003 | Kung et al. |
| 6,643,548 B1 | 11/2003 | Mai et al. |
| 6,808,483 B1 | 10/2004 | Ortiz et al. |
| 6,808,484 B1 | 10/2004 | Peters et al. |
| 6,984,201 B2 | 1/2006 | Khaghani et al. |
| 7,169,109 B2 | 1/2007 | Jansen et al. |
| 7,306,558 B2 | 12/2007 | Peters et al. |
| 7,347,811 B2 | 3/2008 | Peters et al. |
| 7,357,771 B2 | 4/2008 | Peters et al. |
| 7,513,864 B2 | 4/2009 | Kantrowitz et al. |
| 7,616,990 B2 | 11/2009 | Chavan et al. |
| 7,738,965 B2 | 6/2010 | Phillips et al. |
| 7,740,575 B2 | 6/2010 | Peters et al. |
| 7,765,003 B2 | 7/2010 | Peters et al. |
| 8,002,691 B2 | 8/2011 | Peters et al. |
| 2001/0016676 A1 | 8/2001 | Williams et al. |
| 2003/0078634 A1 | 4/2003 | Schulman et al. |
| 2003/0105497 A1 | 6/2003 | Zhu et al. |
| 2003/0233023 A1 | 12/2003 | Khaghani et al. |
| 2004/0010180 A1 | 1/2004 | Scorvo |
| 2004/0073080 A1 | 4/2004 | Peters et al. |
| 2004/0097783 A1 | 5/2004 | Peters et al. |
| 2004/0097784 A1 | 5/2004 | Peters et al. |
| 2004/0147803 A1 | 7/2004 | Hedge et al. |
| 2004/0152945 A1 | 8/2004 | Kantrowitz et al. |
| 2004/0162585 A1* | 8/2004 | Elghazzawi et al. ............. 607/5 |
| 2006/0052866 A1 | 3/2006 | Gilles et al. |
| 2006/0085039 A1 | 4/2006 | Hastings et al. |
| 2007/0021830 A1 | 1/2007 | Peters |
| 2007/0060787 A1* | 3/2007 | Peters et al. .................. 600/17 |
| 2007/0093684 A1 | 4/2007 | Peters et al. |
| 2007/0129796 A1 | 6/2007 | Miller |
| 2007/0135677 A1 | 6/2007 | Miller et al. |
| 2007/0167898 A1 | 7/2007 | Peters et al. |
| 2007/0255350 A1 | 11/2007 | Torgerson |
| 2008/0027270 A1 | 1/2008 | Peters et al. |
| 2008/0139873 A1 | 6/2008 | Peters et al. |
| 2008/0161795 A1 | 7/2008 | Wang et al. |
| 2008/0167515 A1 | 7/2008 | Peters et al. |
| 2008/0194905 A1 | 8/2008 | Walsh |

(56) References Cited

U.S. PATENT DOCUMENTS

| | | |
|---|---|---|
| 2008/0266748 A1 | 10/2008 | Lee |
| 2009/0054949 A1 | 2/2009 | Alexander et al. |
| 2009/0118826 A1 | 5/2009 | Khaghani |
| 2009/0149950 A1 | 6/2009 | Wampler |
| 2009/0204170 A1 | 8/2009 | Hastings et al. |
| 2009/0276016 A1 | 11/2009 | Phillips et al. |
| 2010/0016835 A1 | 1/2010 | Davey |
| 2010/0191036 A1 | 7/2010 | Sullivan |
| 2010/0256440 A1 | 10/2010 | Maher |
| 2010/0292528 A1 | 11/2010 | De Plater |
| 2010/0292629 A1 | 11/2010 | Dacey, Jr. et al. |
| 2010/0324354 A1 | 12/2010 | Peters |
| 2011/0166630 A1 | 7/2011 | Phillips et al. |
| 2011/0270331 A1 | 11/2011 | Peters et al. |
| 2011/0275883 A1 | 11/2011 | Peters |
| 2011/0288367 A1 | 11/2011 | Miller |
| 2011/0298304 A1 | 12/2011 | Cotter |
| 2011/0301668 A1 | 12/2011 | Forsell |
| 2012/0065457 A1 | 3/2012 | Peters et al. |
| 2012/0095280 A1 | 4/2012 | Timms |
| 2012/0305603 A1 | 12/2012 | Kwok et al. |

FOREIGN PATENT DOCUMENTS

| | | |
|---|---|---|
| EP | 0217964 | 4/1987 |
| EP | 0080348 B2 | 5/1988 |
| EP | 0363203 | 4/1990 |
| EP | 0364799 | 4/1990 |
| EP | 0216042 | 3/1991 |
| EP | 0601804 | 6/1994 |
| EP | 0583012 | 7/1996 |
| EP | 0547733 | 4/1998 |
| EP | 1129736 | 9/2001 |
| FR | 2458288 | 1/1981 |
| FR | 2645739 | 10/1990 |
| FR | 2767874 | 3/1999 |
| GB | 2422114 | 4/2008 |
| JP | H6-510461 | 11/1994 |
| JP | 9-502376 | 3/1997 |
| JP | 9-503933 | 4/1997 |
| JP | 10-328297 | 12/1998 |
| JP | H11-285529 | 10/1999 |
| JP | 2000-000299 | 1/2000 |
| JP | 2000-510006 | 8/2000 |
| JP | 2001-276213 | 10/2001 |
| JP | 2003-135497 | 5/2003 |
| WO | WO 90/15630 | 12/1990 |
| WO | WO 92/08500 | 5/1992 |
| WO | WO 93/08874 | 5/1993 |
| WO | WO 95/05122 | 2/1995 |
| WO | WO 95/28127 | 10/1995 |
| WO | WO9624395 | 8/1996 |
| WO | WO 97/40755 | 11/1997 |
| WO | WO 98/05289 | 2/1998 |
| WO | WO 98/14239 | 4/1998 |
| WO | WO 98/51367 | 11/1998 |
| WO | WO 99/02213 | 1/1999 |
| WO | WO 99/04833 | 2/1999 |
| WO | WO 99/45981 | 9/1999 |
| WO | WO 00/12168 | 3/2000 |
| WO | WO 00/76288 | 12/2000 |
| WO | WO 01/13974 | 3/2001 |
| WO | WO 01/83001 | 11/2001 |
| WO | WO 02/24254 | 3/2002 |
| WO | WO 02/24255 | 3/2002 |
| WO | WO 02/076305 | 10/2002 |
| WO | WO 03/011365 | 2/2003 |
| WO | WO 03/028787 | 4/2003 |
| WO | WO 2004037152 A2 | 5/2004 |
| WO | WO 2004/045677 | 6/2004 |
| WO | WO 2005/041783 | 5/2005 |
| WO | WO 2005/042063 | 5/2005 |
| WO | WO 2005/042089 | 5/2005 |
| WO | WO 2005/044338 | 5/2005 |
| WO | WO 2008/053469 | 5/2005 |
| WO | WO2005042089 A1 | 5/2005 |
| WO | WO 2005/110512 | 11/2005 |
| WO | WO 2008/071223 | 6/2008 |
| WO | WO 2011/098769 | 8/2011 |

OTHER PUBLICATIONS

J.L. Stewart, "Aortic Cuff a Cardiac Assistance Device", Polytechnic Institute of Brooklyn, 1968, pp. 9-108.

Hiroshi Odaguchi et al., "Experimental Study of Extraaortic Balloon Counterpulsation as a Bridge to Other Mechanical Assists" ASAIO Journal, pp. 190-194, vol. 42, No. 3, Lippincott Williams & Wilkins/ASAIO, Hagerstown, MD, May 1, 1996.

"Use of Heart Valve Sounds as Input to Cardiac Assist Devices", Research Disclosures, Mar. 1995.

Luisada et al., On the Function of the Aortic Valve and the Mechanism of the First and Second Sounds, Japanese Heart Journal, vol. 18(1), Jan. 1977, pp. 81-91.

International Search Report issued in PCT/AU00/00654, mailed Aug. 18, 2000, 5 pages.

International Search Report issued in PCT/AU2002/000974, mailed Oct. 11, 2002, 5 pages.

International Preliminary Examination Report issued in PCT/AU2002/000974, completed Aug. 11, 2003, 8 pages.

International Search Report issued in PCT/AU2001/01187, mailed Nov. 5, 2001, 3 pages.

International Preliminary Examination Report issued in PCT/AU2001/01187, completed May 2, 2002, 4 pages.

International Search Report and Written Opinion issued in PCT/AU2007/001188, mailed Oct. 4, 2007, 12 pages.

International Preliminary Report on patentability, Chapter II, issued in PCT/AU2007/001188, completed Mar. 11, 2008, 8 pages.

International Search Report issued in PCT/AU2003/001450, mailed Feb. 2, 2004, 2 pages.

International Preliminary Examination Report issued in PCT/AU2003/001450, completed Mar. 2, 2005, 4 pages.

International Search Report issued in PCT/AU2003/001458, mailed Feb. 5, 2004, 5 pages.

International Prelminary Examination Report issued in PCT/AU2003/001458, completed Mar. 7, 2005, 7 pages.

International Search Report and Written Opinion issued in PCT/AU2004/001483, mailed Nov. 26, 2004, 5 pages.

International Search Report and Written Opinion issued in PCT/AU2004/001484, mailed Nov. 29, 2004, 5 pages.

International Search Report and Written Opinion issued in PCT/AU2004/01485, mailed Feb. 7, 2005, 6 pages.

International Search Report and Written Opinion issued in PCT/AU2004/001486, mailed Jan. 6, 2005, 7 pages.

International Search Report and Written Opinion issued in PCT/AU2004/01487, mailed Jan. 27, 2005, 12 pages.

International Search Report and Written Opinion issued in PCT/AU2004/01488, mailed Dec. 15, 2004, 6 pages.

Supplemental European Search Report issued in EP Application 00934813, mailed 0/19/2006, 2 pages.

Supplemental European Search Report issued in EP 01971489, completed Nov. 22, 2006, 4 pages.

Supplemental European Search Report issued in EP App No. 02748447, Feb. 6, 2007, 6 pages.

Supplemental European Search Report issued in EP App. No. 04789624, mailed Mar. 6, 2008, 7 pages.

Supplemental European Search Report issued in EP 04789625, mailed Nov. 18, 2009, 6 pages.

Office Action issued in JP Application No. 2004-552261, dated Mar. 2, 2010.

Office Action issued in JP Application No. 22006-53700, dispatched Jun. 22, 2010, with English translation, 12 pages.

Hemodynamic and Metabolic Effects of Para—versus Intraaortic Counterpulsatile Circulation Supports.

* cited by examiner

COMBINATION HEART ASSIST SYSTEMS, METHODS, AND DEVICES

CROSS-REFERENCE TO RELATED APPLICATION

This application is a divisional of U.S. application Ser. No. 13/078,666, filed on Apr. 1, 2011 and entitled Combination Heart Assist Systems, Methods, and Devices, which claims priority to U.S. Provisional Patent Application No. 61/320, 549, filed on Apr. 2, 2010, both of which are incorporated herein by reference in their entireties.

FIELD OF THE INVENTION

The various embodiments disclosed herein relate to methods and devices for controlling the operation of a mechanical heart assist device or controlling the operation of both a mechanical heart device and an electrical therapy device.

BACKGROUND OF THE INVENTION

Heart failure is a degenerative disease that leads to decreased cardiac output that is highly symptomatic, with significant quality of life issues for the patient. Treatment beyond drugs includes cardiac resynchronization therapy (CRT), cardiac assist therapy such as LVAD (left ventricular assist device), and ultimately heart transplant. Resynchronization control of the left and right ventricles of the heart provided by CRT therapy in heart failure patients has proven benefits, including safety, improvements in quality of life, and reductions in hospitalization and NYHA Class heart failure levels. However, CRT therapy is only applicable to a subset of heart failure patients and a large percentage of heart failure patients who initially appear to be suitable for treatment with CRT therapy are "non-responders" to the demonstrated benefits. Less than 30% of heart failure patients are considered for CRT treatment and non-responders are reported to be 25% to 45% of patients treated.

A number of mechanical cardiac assist devices are used to treat heart failure patients. Such devices include both pulsatile devices that operate in timed synchrony with the heart and non-pulsatile devices that run without any such synchronization. For example, counter-pulsation heart assist devices such as those disclosed in the Applicants' U.S. Pat. No. 6,808,484, issued Oct. 26, 2004 and entitled "Heart Assist Devices, Systems and Methods," which is hereby incorporated herein by reference in its entirety, are configured to compress the aorta in synchrony with the diastolic period, the beginning of which is marked by closure of the aortic valve to reduce the interior volume of the aorta during diastole. This compression increases systemic blood pressure, increases blood flow through the coronary arteries and increases diastolic output against the closed aortic valve. Release of the compression timed to the r wave and beginning of systole provides left ventricular unloading and improved native contractility of the heart muscle.

Other pulsatile heart assist devices include co-pulsation devices, which are configured to compress the heart in synchrony with the contraction of the ventricles or filling of the aorta. One example of a co-pulsation device is a right ventricular co-pulsation assist device, such as the devices described in U.S. Pat. No. 4,690,134 or U.S. Pat. No. 5,169,381. Co-pulsation devices are triggered in synchrony with the ventricular depolarization to assist the cardiac output. Co-pulsation assist devices have been described for both the left and right ventricles and reduced to practice in animal studies such as "Copulsation Balloon for Right Ventricular Assistance: Preliminary Trials;" Circulation, 99:2815-2818 (1999). As in counter-pulsation, the timing with the native rhythm must be precise for maximum effectiveness.

There is a need in the art for improved methods, devices, and systems for controlling the operation of a pulsatile heart assist device or controlling the operation of both a pulsatile heart device and an electrical therapy device (such as, for example, a CRT pacemaker) for various types of cardiac therapies.

BRIEF SUMMARY OF THE INVENTION

Discussed herein are various cardiac therapy configurations for providing cardiac assistance, including various systems, methods, and devices having both an electrical therapy device and a mechanical heart assist device.

In Example 1, a heart assist system comprises a mechanical heart assist device, a controller operably coupled to the mechanical heart assist device, and an electrical therapy device operably coupled to the controller. The controller is configured to transmit an actuating signal to the mechanical heart assist device. The electrical therapy device has at least one sensor operably coupled to the electrical therapy device and at least one pacing component operably coupled to the electrical therapy device. The at least one sensor is configured to detect a heart characteristic and transmit a signal relating to the heart characteristic to the electrical therapy device. The at least one pacing component is configured to pace the heart.

Example 2 relates to the system according to Example 1, wherein the sensor is a sensing lead, wherein the sensing lead is configured to be positionable in or adjacent to the heart.

Example 3 relates to the system according to Example 1, wherein the sensor is physically integral with the electrical therapy device.

Example 4 relates to the system according to any of Examples 1-3, wherein pacing component is a pacing lead, wherein the pacing lead is configured to be positionable in or adjacent to the heart.

Example 5 relates to the system according to any of Examples 1-3, wherein the pacing component is physically integral with the electrical therapy device.

Example 6 relates to the system according to any of Examples 1-5, wherein the controller is physically integral with the electrical therapy device.

Example 7 relates to the system according to any of Examples 1-5, wherein the controller is physically integral with the mechanical heart assist device.

Example 8 relates to the system according to any of Examples 1-7, wherein the mechanical heart assist device is a pulsatile device.

Example 9 relates to the system according to any of Examples 1-8, wherein the electrical therapy device is an implantable cardiac resynchronization therapy and defibrillation device ("CRT-D").

Example 10 relates to the system according to any of Examples 1-8, wherein the electrical therapy device is an implantable cardioverter-defibrillator device ("ICD").

Example 11 relates to the system according to any of Examples 1-10, wherein the sensor is an electrical sensing lead configured to sense a loss or reduction of ventricular contraction and transmit information to the electrical therapy device, wherein the electrical therapy device is configured to transmit an actuating signal to the controller, wherein the controller is configured to transmit an actuating signal to the mechanical heart device to operate to provide circulatory support until the heart is defibrillated or normal cardiac rhythm is restored.

Example 12 relates to the system according to any of Examples 1-10, wherein the sensor is an electrical sensing lead configured to sense a loss or reduction of ventricular contraction and transmit information to the electrical therapy device, wherein the electrical therapy device is configured to transmit an actuating signal to the controller, wherein the controller is configured to transmit an actuating signal to the mechanical heart device to operate to provide circulatory support until the electrical therapy device defibrillates the heart.

Example 13 relates to the system according to any of Examples 1-10, wherein the electrical therapy device is configured to actuate the at least one pacing component to electrically stimulate a ventricle of the heart in synchronization with the controller being configured to actuate the mechanical heart assist device.

Example 14 relates to the system according to any of Examples 1-13, wherein the sensor is chosen from a group consisting of an electrical sensor; an ECG sensor; heart vibration sensor, a heart acoustics sensor, a flow sensor, a pressure sensor, an impedance sensor, a wall stress sensor, and an optical reflectance sensor, wherein the sensor is positionable within or adjacent to the heart or a great vessel of the heart.

Example 15 relates to the system according to any of Examples 1-13, wherein the sensor is an acoustic sensor, wherein the acoustic sensor is an aortic valve acoustic sensor configured to detect sounds of an aortic valve in the heart.

In Example 16, a method of controlling a heart assist device comprises detecting a characteristic of a heart with a sensor, transmitting about a signal relating to the heart characteristic to an electrical therapy device via the sensor, and actuating the electrical therapy device to transmit a pacing signal to a pacing component based at least in part on the heart characteristic signal. The method also includes transmitting characteristic signal to a controller and actuating a mechanical heart assist device with an actuating signal from the controller, wherein the transmitting the signal to the controller is based at least in part on the heart characteristic signal and wherein the actuating is based at least in part on the signal to the controller.

Example 17 relates to the method according to Example 16, wherein the transmitting the signal to the controller further comprises transmitting the signal to the controller via a connecting lead coupled to the electrical therapy device and the controller.

Example 18 relates to the method according to Examples 16 or 17, wherein the sensor is a sensing lead.

Example 19 relates to the method according to any of Example 16-18, wherein the pacing component is a pacing lead.

Example 20 relates to the method according to any of Examples 16-19, wherein the controller is physically integral with the electrical therapy device.

Example 21 relates to the method according to any of Examples 16-19, wherein the controller is physically integral with the mechanical heart assist device.

Example 22 relates to the method according to any of Examples 16-21, wherein the mechanical heart assist device is a pulsatile device.

Example 23 relates to the method according to any of Examples 16-22, further comprising actuating both the mechanical heart assist device and the electrical therapy device to operate synchronously to assist the heart based on the information about the heart characteristic.

Example 24 relates to the method according to any of Examples 16-23, wherein the heart characteristic comprises a loss or reduction of ventricular contraction, wherein the actuating the electrical therapy device further comprises actuating the electrical therapy device to transmit a defibrillation discharge to the heart via a ventricular lead based on the information about the heart characteristic, and wherein the actuating the mechanical heart assist device further comprises actuating the mechanical heart assist device to provide circulatory support until the heart is defibrillated or normal cardiac rhythm is restored.

Example 25 relates to the method according to any of Examples 16-23, wherein the heart characteristic comprises a loss or reduction of ventricular contraction, wherein the actuating the electrical therapy device further comprises actuating the electrical therapy device to transmit a defibrillation discharge to the heart via a ventricular lead based on the information about the heart characteristic, and wherein the actuating the mechanical heart assist device further comprises actuating the mechanical heart assist device to provide circulatory support until the electrical therapy device transmits the defibrillation charge to the heart.

Example 26 relates to the method according to any of Examples 16-25, wherein the electrical therapy device is an ICD.

Example 27 relates to the method according to any of Examples 16-25, wherein the electrical therapy device is a CRT-D.

Example 28 relates to the method according to any of Examples 16-22, 26, or 27, wherein the actuating the electrical therapy device and the actuating the mechanical heart assist device further comprises synchronously actuating the mechanical heart assist device to operate the aortic compression structure to compress the ascending aorta while actuating the electrical therapy device to transmit the pacing signal to the heart via the pacing component, whereby the mechanical heart assist device and the electrical therapy device operate in conjunction to assist the heart.

Example 29 relates to the method according to any of Examples 16-28, wherein the heart characteristic is chosen from the group consisting of heart vibrations, heart sounds, flow, pressure, impedance, wall stress, and optical reflectance.

In Example 30, a method of assisting and strengthening a heart comprises detecting a characteristic of a heart with a sensing lead, transmitting information about the heart characteristic to an electrical cardiac therapy device via the sensing lead, and actuating the electrical cardiac therapy device based at least in part on the information about the heart characteristic. The method further includes transmitting the information about the heart characteristic to a controller via a connecting lead coupled to the electrical cardiac therapy device and the controller and actuating an implantable mechanical heart assist device with an actuating signal from the controller, wherein the actuating is based at least in part on the information about the heart characteristic. In addition, the method includes periodically timing the actuating of the mechanical heart assist device and the electrical cardiac therapy device such that a predetermined amount of resistance to contraction is created in the heart.

Example 31 relates to the method according to Example 30, wherein the electrical cardiac therapy device is an ICD.

Example 32 relates to the method according to Example 30, wherein the electrical cardiac therapy device is a CRT-D.

Example 33 relates to the method according to any of Examples 30-32, wherein the periodically timing the actuating of the mechanical heart assist device and the electrical cardiac therapy device further comprises timing the actuating of the devices such that the predetermined amount of resistance to contraction is created in the heart for a predetermined treatment period each day.

Example 34 relates to the method according to Example 33, further comprising increasing or decreasing the predetermined treatment period as the heart is strengthened.

Example 35 relates to the method according to either Example 33 or 34, further comprising increasing or decreasing the predetermined treatment period after a predetermined amount of time. While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

In Example 36, a method of controlling a heart assist device comprises detecting a characteristic of a heart with a sensor, transmitting about a signal relating to the heart characteristic to an electrical therapy device via the sensor, and actuating the electrical therapy device to transmit a signal to a lead based at least in part on the heart characteristic signal. The method also includes transmitting a signal to a controller and actuating a mechanical heart assist device with an actuating signal from the controller, wherein the transmitting the signal to the controller is based at least in part on the heart characteristic signal and wherein the actuating is based at least in part on the signal to the controller.

Example 37 relates to the method according to Example 36, wherein the signal is a pacing signal.

Example 38 relates to the method according to Example 36, wherein the signal is a defibrillation signal.

DETAILED DESCRIPTION

The various embodiments and inventions disclosed herein relate to methods, devices, and systems for controlling the operation of a mechanical heart assist device, such as, for example, a pulsatile heart assist device and an electrical therapy device. For example, various embodiments disclosed herein relate to controlling the operation of pulsatile heart assist devices such as, for example, the various devices disclosed in U.S. Pat. No. 6,808,484 mentioned above, in combination with an electrical therapy device such as an ICD or CRT-D device. Other embodiments discussed herein are also suitable for use in controlling other heart assist devices, including, but not limited to, intra-aortic balloons, aortomyoplasty, other counter- and co-pulsation devices, pacemakers, defibrillators, cardiac cycle monitoring, or left ventricular assist devices. Still other embodiments relate to controlling any combination of these various devices.

The methods, devices, and systems contemplated herein relate to detection of at least one of certain points in the cardiac cycle for use in timing counter and co-pulsation heart assist devices. Various embodiments of these methods, devices, and systems can assist the heart during congestive heart failure, provide emergency circulatory support during a cardiac event, or provide programmed resistance training to the heart during heart failure recovery. Certain embodiments relate to methods, devices, and systems having either an electrical sensing lead that is used to control a mechanical heart assist device and an electrical heart assist device such as a combination internal defibrillation and cardiac resynchronization therapy device ("ICD/CRT device") that are directly or indirectly interconnected. In these embodiments, the ICD/CRT device can be used for pacing the heart or alternatively for defibrillation, while the mechanical heart assist device can be used for assisting the heart (alone or in combination with the ICD/CRT device) or for providing "internal CPR" to the heart during ventricular fibrillation ("VF") or asystole while the ICD/CRT is charging for defibrillation. Alternative embodiments have an ICD/CRT device that can be used as a sensing lead to detect electrical cardiac signals that are then used to control a heart assist device while also being used for pacing the heart or alternatively for defibrillation.

Figure 1:
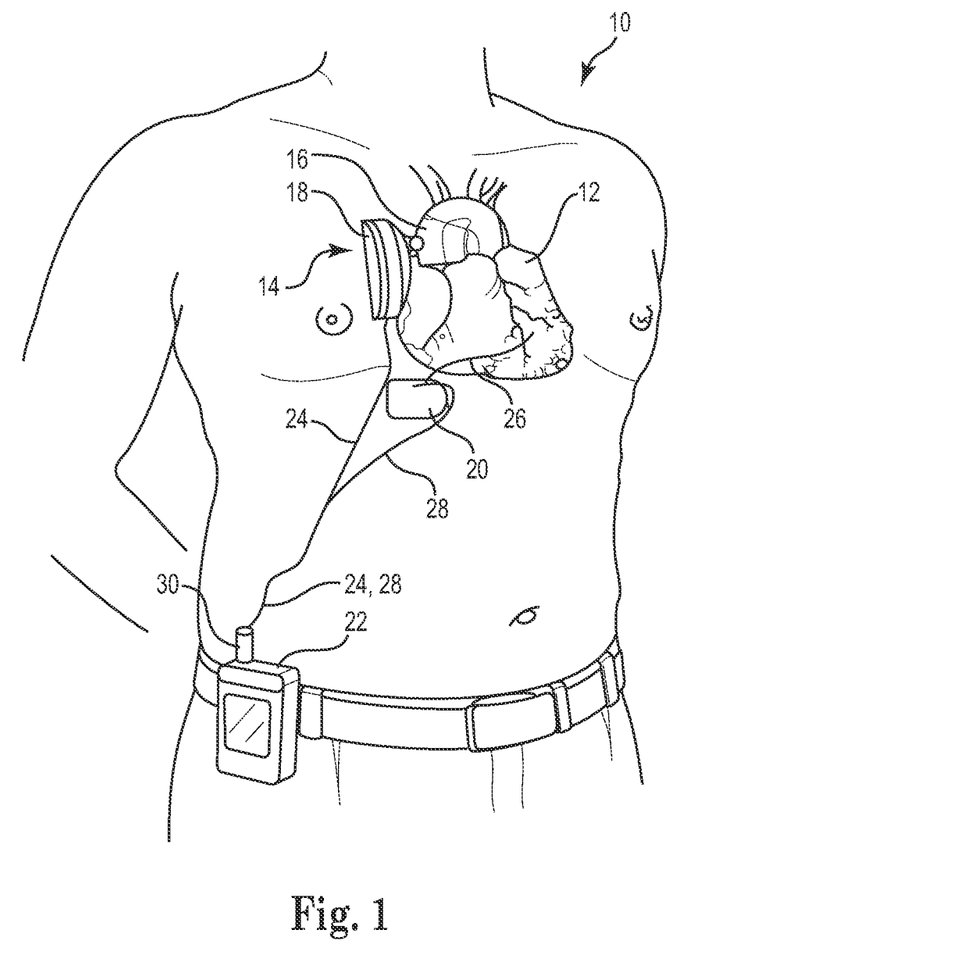
FIG. 1 is a cut away view of a patient with a combination heart assist system, in accordance with one embodiment.

FIG. 1 depicts a patient 10 with a heart 12. The output of the heart 12 is assisted by a pulsatile implantable heart assist device 14. In one embodiment, the heart assist device 14 has an aortic cuff 16 around the patient's ascending aorta. Various examples of heart assist devices having aortic cuffs that could be used in the various embodiments described herein are set forth in U.S. Pat. No. 7,306,558, issued on Dec. 11, 2007 and entitled "A Fluid Pressure Generating Means," which is hereby incorporated herein by reference in its entirety. Alternatively, any known pulsatile heart assist device can be used. In this embodiment, the cuff 16 is driven by a pump 18. The pump 18 is powered/controlled by an external battery/controller 22 via a percutaneous electrical cable 24.

This embodiment also has a pacemaker 20. In one exemplary implementation, the pacemaker 20 is a dual-chamber pacemaker 20 such as model S603 of the ALTRUA™ family of pacemakers, which is commercially available from Boston Scientific Corp. of St Paul, Minn., USA. Alternatively, any known pacemaker can be used in this embodiment. The pacemaker 20 has an atrial circuit connected to sensing lead 26 and thereby to the ventricle of the heart 12, and a ventricular circuit connected to the controller 22 through an electrical cable 28.

In operation, according to one embodiment, after receiving a ventricular rhythm signal (ie. the R wave of the ventricle) through the atrial circuit, the pacemaker 20 may wait for a predetermined time and then issue a pacing signal to the controller 22, which in turn controls the pulsation of the heart assist device 14. Alternatively, the pacemaker 20 can issue the pacing signal immediately (without any predetermined delay). It will be understood that, in the above configuration, the pacemaker 20 typically issues the pacing signal to the controller 22 as the controller 22 cannot issue the signal indicative of ventricular rhythm that the pacemaker 20 is awaiting. If desired, the pacemaker 20 may issue the pacing signal from the ventricular circuit immediately upon receiving the sensed signal in the atrial circuit. In this case, there would be a delay built into the controller 22 to ensure that the time at which the heart assist device 14 is actuated is correctly correlated with the native heart rhythm.

According to one embodiment, the pacemaker 20 can be adjusted to control a heart assist device in accordance with a patient's needs by using available programmers. Further, pacemakers are normally designed to allow correct sensing of cardiac activity even in the presence of electrical interference. They are normally designed to withstand defibrillation pulses without damage.

In the embodiment shown, the heart assist device 14 is a counter pulsation device in which the pulsations are out of phase with the heart's native rhythm. The atrial circuit of the pacemaker 20 is normally adapted to sense the P wave of the atrium but, in this particular embodiment, it instead senses the R wave of the ventricle as described above and transmits the signal to the controller 22, which thereby synchs the actuation of the pulsatile device 14.

According to one implementation, an optically coupled isolator 30 can be placed in the cable 28 to electrically isolate the pacemaker 20 from the controller 22. The isolator 30 converts the pacing signal produced by the ventricular circuit of the pacemaker into a light signal which is then returned to an electrical signal which is conveyed to the controller 22. The isolator prevents electrical signals being conveyed from, or through, the controller 22 to the heart 12. One commercially-available example of a suitable type of isolator is the OPI110 line of isolators, available from Optek Technology Inc of Carrollton, Tex. Alternatively, the electrical device 20 (or any other electrical device according to any of the embodiments disclosed herein) can have a optical output channel that outputs an optical signal (instead of an electrical signal) via a fiber optic cable such as that disclosed in U.S. Pat. No. 6,925,328 (which is hereby incorporated herein by reference in its entirety) for device-to-device communication, such that the isolator 30 is not necessary.

Figures 2A, 2B:
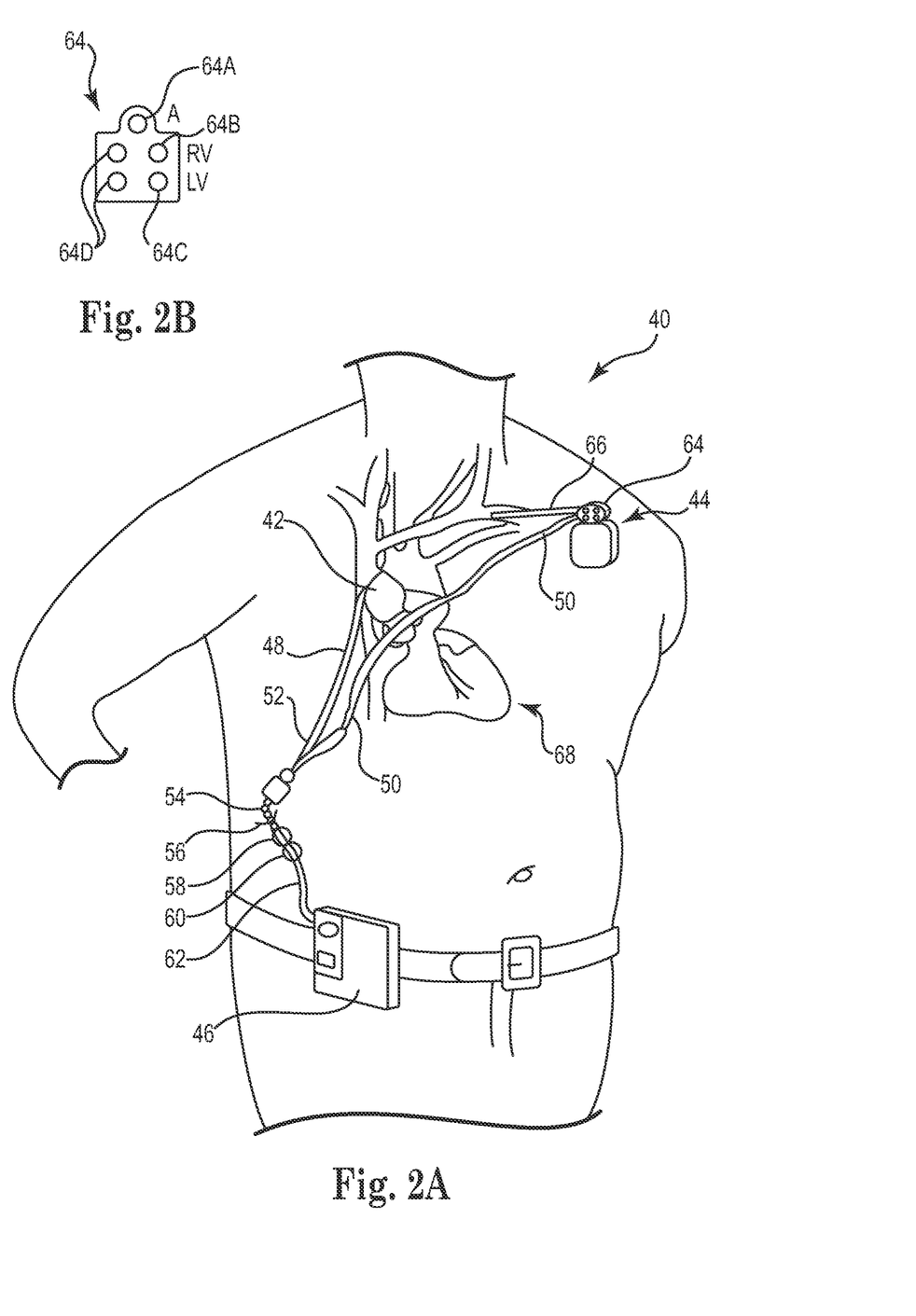
FIG. 2A is a cut away view of a patient with a combination heart assist system, according to another embodiment.
FIG. 2B is a side view of a connection header block for the electrical therapy device incorporated into the combination heart assist system embodiment of FIG. 2A.

FIGS. 2A and 2B depict another embodiment relating to a system and method 40 having both a pulsatile implantable heart assist device 42 and an electrical therapy device 44. In one embodiment, the electrical therapy device 44 is a cardiac resynchronization therapy device ("CRT"). Alternatively, the electrical therapy device 44 is an implantable cardioverter defibrillator ("ICD"). In a further embodiment, the electrical therapy device 44 is a combined CRT-ICD device (also known as a "CRT-D"). In the remainder of the description relating to FIG. 2A (and the embodiments in the additional figures and the related description herein), it will be assumed that the electrical device 44 is a CRT-D device, with the understanding that other known electrical therapy devices can be incorporated into various embodiments of the system. The output of the heart 68 is assisted by the pulsatile device 42 and the electrical therapy device 44 using various operational modes as described in further detail below.

In one embodiment, the heart assist device 42 is an aortic cuff 42 around the patient's ascending aorta. It is understood that any pulsatile devices disclosed in the '558 patent described and incorporated by reference above or any other known pulsatile heart assist devices can be used.

The pulsatile device 42 and the electrical device 44 are both coupled to an external driver/controller 46. More specifically, the pulsatile device 42 is coupled via a drive line 48 to a pump (not shown) in the driver/controller 46. The electrical device 44 is coupled to the driver/controller 46 via an electrical lead 50. As shown in FIG. 2A, in one embodiment the drive line 48 and electrical lead 50 extend from the pulsatile device 42 and the electrical device 44, respectively, to a "Y" connector 52. At the "Y" connector 52, the drive line 48 and electrical lead 50 are positioned within an internal device coupling cable 54. The cable extends from the "Y" connector 52, through an incision 56 in the patient, and to a first connector 58 positioned outside the patient. The first connector 58 is removably coupled to a second connector 60 at one end of an external device coupling cable 62 that extends from the second connector 60 to the driver/controller 46. In this configuration, the drive line 48 extends from the pulsatile device 42, through the "Y" connector 52, through the incision 56, through the connection of first connector 58 and the second connector 60, and to the pump (not shown) in the driver/controller. Similarly, the electrical lead extends from the electrical device 44, through the "Y" connector 52, through the incision 56, through the connection of first connector 58 and the second connector 60 and to the driver/controller. Alternative implementations of the systems contemplated herein do not have a "Y" connector. Instead, the pulsatile device 42 and the electrical device 44 can be coupled to the controller by any known structures or components.

In this embodiment, the cuff 42 is driven by the pump (not shown) in the driver/controller 46 via the drive line 48. In this implementation, the drive line 48 is an air line 48. In an alternative configuration, the pump can be a separate unit that is located anywhere on the system so long as it is coupled to the device 42. According to one implementation, the pump is one of any of the programmable pumps that can be driven in a controlled manner with adjustable pressure, volume and slew rate and are well known in the art. One example of a pump that can be incorporated into the driver/controller 46 is described in further detail in U.S. Pat. No. 7,306,558, which is incorporated by reference and discussed above, in which the pump is a fluid-filled chamber with a reciprocating piston driven by a screw drive motor but located wholly within external driver/controller 46 and coupled to air line 48. Alternatively, the pump can be a reciprocating piston and a diaphragm bellows driven by an electric motor and coupled to air line 48. Other types of pumps that can be used in the driver/controller 46 include turbine compressors, piezoelectric motors, linear motors, ultrasonic motors, or compressed gas.

The driver/controller 46 also has a power source (not shown). In one embodiment, the power source is an electric power source such as a battery, solar, wireless RF, or inductively-coupled coils. Alternatively, the power source can be a pneumatic power source such as liquid $CO_2$.

In one embodiment, the connector lead 50 is any known lead that can couple two components. For example, in one embodiment, the connector lead 50 is a known interconnect IS-1 to IS-1 connector cable 50 that is commercially available from such companies as Oscor Inc. of Palm Harbor, Fla. Alternatively, the connector lead 50 can be a dual-purpose lead that is configured to transport not only a normal pacing trigger signal (to the controller 46, for example), but also an encoded digital signal or a multiplexed signal containing both a DC and AC or RF component waveform. In one implementation, the combined waveform could be used to control the pulsatile device 42 and thus simplify the digital processing load for the controller 46. In a further alternative, the combined waveform could be used to transfer sensed information to the controller 46 (such as, for example, information relating to various modes described in further detail below, including emergency CPR support mode, increased activity mode, larger stroke volume required, or reduced activity mode for lower stroke volume).

The electrical therapy device 44 in FIG. 2A has a connection header block 64. In one embodiment, the connection header block 64 has the configuration depicted in FIG. 2B with five ports 64A, 64B, 64C, and 64D as described below. Alternatively, it is understood that the connection header block 64 used in this particular embodiment or any other embodiment contemplated herein can be any known header block 64. For example, in certain embodiments, a six-port header block (that is, the block has six ports) is used. The header block 64 in FIG. 2B defines female connection lumens (also referred to herein as "ports") 64A, 64B, 64C, and 64D, which are configured to receive electrical sensing and pacing leads to be coupled to the device 44. For example, in one implementation, port 64B as shown in FIG. 2B is configured to receive a connector for the right ventricular lead 66 as shown in FIG. 2A. Similarly, additional sensing and/or pacing leads can be connected to the header block 64. As best shown in FIG. 2B, according to one implementation in which the electrical device is a CRT-D, the port 64A is configured to receive a connector for an atrial lead (not shown), port 64C is configured to receive a connector for the connector lead 50 coupled to the controller 46, and the two ports 64D are configured to receive additional connectors for the superior vena cava electrode and the defibrillation electrode (not shown) in the right ventricular lead. Alternatively, the ports in the header block 64 can be configured to receive any known arrangement of leads as appropriate for any particular type of electrical therapy device 44. It is understood that the right ventricular lead 66 and the atrial lead (not shown) coupled to the device 44 at the header block 64 are positioned through a vessel such as the subclavian vein and ultimately in a predetermined location in the heart. More specifically, the distal end of the right ventricular lead 66 is positioned in the right ventricle and the atrial lead (not shown) is positioned in the atrium. It is further understood that the connection lead 50 extends from the header block 64 to the "Y" connector 52 as described in further detail above.

In one exemplary embodiment, the electrical therapy device 44 is a known dual chamber implantable cardioverter defibrillator with cardiac resynchronization therapy (CRT-D), and in a more specific implementation is Model D274TRK Concerto II CRT-D, which is commercially available from Medtronic Inc. of Minneapolis, Minn. USA. This device in this embodiment is a multiprogrammable cardiac device that monitors and regulates the patient's heart rate by providing single or dual chamber rate-responsive bradycardia pacing, sequential biventricular pacing, ventricular tachyarrhythmia therapies, and atrial tachyarrhythmia therapies. As in the embodiment described above, this specific CRT-D device 44 has an IS-1 header block for connection to the counterpulsation controller 46. In one exemplary operation, the Concerto II CRT-D device 44 can respond to a bradyarrhythmia by providing bradycardia pacing therapies that will also drive the assist device controller 46 at a programmed rate.

In accordance with one implementation, the system 40 (or any other system embodiments described herein) can be constructed based on an existing standard electrical pacing system that has already been implanted into a patient. More specifically, it is anticipated that one typical use of the system embodiments having both electrical and pulsatile assistance as contemplated herein would be in the setting of a patient having an existing, implanted electrical therapy device who is a failed CRT case or a "non-responder" and requires or could benefit from additional cardiac assistance. That is, the patient has a standard electrical pacing system including the electrical therapy device 44 and the atrial, left, and right ventricular leads, but for some reason the electrical therapy has not been successful or sufficient. Thus, for various reasons, it may be beneficial to the patient to add a pulsatile device 42 to create the system 40 as depicted in FIG. 2 without changing the operation of the electrical therapy device that was previously implanted. This can be accomplished by implanting the device 42 with the drive line 48, coupling the connector lead 50 to the header block 64 and the "Y" connector 52, and connecting the controller 46 to the system 40 by coupling the first connector 58 and the second connector 60. In the embodiment depicted in FIG. 2A, the connector lead 50 is coupled to the header block 64 by uncoupling the left ventricular lead from the port 64C and inserting the connector lead 50 into the port 64C in its place. In this implementation, the left ventricular lead can either be removed from the patient, or it can simply be disconnected and remain implanted in the patient. In a further embodiment in which the header block 64 is a six-port header block, the left ventricular lead need not be uncoupled from the block. Alternatively, the entire system 40 (both the electrical therapy device and the mechanical device and associated components) can be implanted at the same time (in those situations in which there is no previously implanted electrical therapy system already in place).

The system 40 as set forth in FIG. 2 provides combined mechanical and electrical cardiac assistance by one of at least four different modes of operation.

In one embodiment, the mode of operation is "synchronized pacing," in which the system 40 provides combined counterpulsation of the aorta (via the heart assist device 42) with direct control by the electrical therapy device 44, thereby resulting in controlled synchronous ventricular and aortic heart assistance. In other words, the electrical therapy device 44 controls the sensing of the heart characteristics and the synchronized operation of both the electrical therapy device 44 and the pulsatile device 42. In this embodiment, the heart assist device 42 provides supplemental cardiac assistance in synchrony with the electrical therapy device 44. More specifically, in one embodiment, the CRT-D 44 senses heart characteristics via the atrial lead (not shown) and/or the right ventricular lead 66 using known technology. For example, the CRT-D 44 can receive information about atrial depolarization via the atrial lead and further can transmit a ventricular rhythm signal (i.e., the R wave of the ventricle) via the right ventricular lead 66. The CRT-D 44 processor then applies a known process used to control the pulsing of atrial lead (not shown) and/or the right ventricular pacing lead 66 to electrically stimulate the heart to beat in a fashion that simulates a normal heartbeat. In a standard electrical cardiac therapy system, a CRT-D typically stimulates the heart to beat in a simulated normal fashion by pulsing the right and left ventricular leads. As is known in the art, depending on intraventricular delay optimization (which is entirely dependent on the specific patient), a CRT-D coupled to both right and left ventricular leads may (1) pulse both leads at the same time, (2) first pulse the right ventricular lead and then the left, or (3) first pulse the left ventricular lead and then the right. In contrast, in the instant embodiment as shown in FIGS. 2A and 2B in which the CRT-D 44 is coupled to a right ventricular lead 66 and the pulsatile device 42 (and is not coupled to a left ventricular lead), the CRT-D 44 can stimulate the heart to beat in a simulated normal fashion by first pulsing the right ventricular lead 66 and then the pulsatile device 42 as described in further detail below. In alternative embodiments of the combination systems as described herein in which the CRT-D has both right and left ventricular leads (such as, for example (but not limited to), FIGS. 3A and 3B as described below or various embodiments in which the CRT-D has a six-port header block), the CRT-D can stimulate the heart to beat in a simulated normal fashion by pulsing the right and left ventricular leads and actuating the pulsatile device to inflate or otherwise compress the aorta (typically after pulsing the right and left leads).

Thus, in addition to its standard, known functions, according to an embodiment relating to synchronized pacing, the CRT-D 44 processor can also control the pulsatile device 42 to provide supplemental pulsatile assistance to the heart. For example, in one implementation, upon receipt of the heart characteristic signal from one or more of the leads (such as the atrial lead and/or right ventricular lead), the CRT-D 44 processor can cause the pulsatile device 42 to inflate by issuing a pacing signal via the electrical lead 50 to the controller 46, which in turn controls the pulsation of the pulsatile device 42.

It is understood that the timing of the actuation of the pulsatile device 42 to compress the aorta typically does not occur at the same time as the pulsing of the right ventricular lead 66 (or the left ventricular lead in those embodiments having such a lead) as described above. Instead, as best explained with respect to those embodiments described herein having both a right ventricular lead (not shown) and a left ventricular lead 108 (such as, for example, the embodiment depicted in FIG. 3), the right and left leads are first pulsed to stimulate the ventricles to contract. Only after the blood has been urged from the left ventricle into the aorta and the aortic valve has closed is the pulsatile device 42 typically actuated to compress the aorta to provide pulsatile assistance to urge the blood out of the aorta and out to the body. As such, for purposes of synchronous operation of the pulsatile device 42 to support or enhance the cardiac assistance provided by the electrical stimulation of the ventricles, the inflation of the pulsatile device 42 should be timed appropriately to ensure that the inflation occurs after the aortic valve is closed. In addition, it is further understood that the timing of the deflation of the pulsatile device 42 to deflate just prior to or when the aortic valve opens (and the left ventricle begins to contract and urge blood into the aorta) can create a pressure-reducing action (also referred to herein as "ventricular unloading") that assists with urging the blood into the aorta, such that the pulsatile device 42 can provide cardiac assistance by pulsing the aorta to force blood to the body and also by deflating when the aortic valve opens to assist with urging blood into the aorta.

In one embodiment, the CRT-D 44 processor can provide the appropriate timing for pulsation of the pulsatile device 42 by waiting for a predetermined time (such as, but not limited to, a ventricle-to-ventricle ("VV") interval delay ranging from 10 to 80 msec) after receiving the heart characteristic information via the atrial and/or right ventricular lead. After the predetermined time, the CRT-D 44 issues—via the lead 50—a pacing signal to the controller 46, which then actuates the pump in the controller 46 to pulsate the pulsatile device 42 via the drive line 48. According to one implementation, the system—either the CRT-D 44 or the controller 46—further compensates for internal timing delays and isovolumetric contraction to provide accurate deflation timing.

In an alternative embodiment, the controller 46 provides the appropriate timing for pulsation of the pulsatile device 42. That is, after receiving the heart characteristic information, the CRT-D 44 processor immediately issues—via the lead 50—a pacing signal to the controller 46. It is the controller 46 in this embodiment that waits for a predetermined time period after receiving the pacing signal before actuating the pump. After the predetermined period of time, the controller 46 actuates the pump, which provides the fluid pressure—via the drive line 48—that actuates the pulsatile device 42.

Regardless of whether the CRT-D 44 or the controller 46 controls the timing, it is understood that the timing of the electrical stimulation via the CRT-D 44 and the mechanical pulsation via the pulsation device 42 must be initially "tuned" or customized for each individual patient. That is, each patient's cardiac characteristics are different and thus the exact timing of the components of the system 40 (and any other system embodiments herein) should be set or adjusted to fit those characteristics. As mentioned above, the ultimate goal is to optimize the timing of the pacing leads and the pulsatile device 42 such that the pacing leads cause the ventricles of the heart to contract as a unified whole (thereby reflecting normal heart operation) and the pulsatile device 42 maximizes the ventricular unloading and assists in circulating blood to the body. As such, any timing of the system 40 components (including any other system depicted and/or disclosed herein) that achieves such operation can be implemented.

According to one implementation, the "synchronized pacing" mode as described above can be particularly effective in treating those patients who do not respond to standard electrical pacing. That is, a substantial percentage of patients (referred to as "non-responders") cannot be successfully treated with standard electrical pacing using a CRT-D (or other type of pacing device) to stimulate ventricular contractions with left and right ventricular leads. As such, the system depicted in FIG. 2 and described above can be used to provide cardiac therapy to such non-responders by combining the mechanical heart assistance (using the pulsatile device 42) with the standard electrical assistance.

According to one alternative variation of the synchronized pacing mode, the system 40 can provide for rate adaptation in which the amount of support by the pulsatile device 42 can be varied according to the heart rate of the patient. For example, in one embodiment, during synchronized pacing, the normal rate of support of the pulsatile device 42 could be 1:2. In other words, the pulsatile device 42 inflates once for every two heartbeats. Alternatively, the normal rate of support could be any desired ratio. In this variation, as the patient's heart rate changes due to the patient's activities, the support rate can be adjusted. In one implementation, the controller 46 processor can be programmed to have a predetermined heart rate level above which the processor sends a signal to the pulsatile device 42 to increase its support rate (for example, to 1:1). Alternatively, the CRT-D 44 processor can be so programmed.

In operation, a patient's heart rate may increase as a result of exercise or any other type of physical exertion. As the heart rate increases, the sensing leads of the CRT-D 44 (such as the atrial and/or right ventricular lead, for example) can detect the increase and provide that information to the CRT-D 44. Then, as discussed above, when the rate increase reaches a predetermined level, either the CRT-D 44 processor or the controller 46 processor can transmit a signal to the pulsatile device 42 to increase its support rate by some predetermined amount (such as, for example, 1:1). Alternatively, the CRT-D 44 processor or the controller 46 processor can transmit a signal to the device 42 to increase its support in any known fashion (such as, for example, increasing the amount of the aortic compression). In further alternative embodiments, the system can also provide for decreasing the support of the pulsatile device 42 by some predetermined amount when the heart rate drops below a certain level (such as, for example, when the patient is sleeping).

Yet another alternative embodiment to the synchronized pacing mode relates to adjusting the amount of support by the pulsatile device 42 based on trans-thoracic impedance. It is known that standard ICD and CRT devices are capable of sensing fluid build-up in the lungs by trans-thoracic impedance measurement. More specifically, the conductivity between the electrical device 44 and a defibrillation electrode on one of the leads is measured on a regular basis. If the conductivity increases over time, that is an indication that the amount of fluid in the lungs has increased, and that information can be transmitted by the CRT-D to some external component for review by a user or a doctor or other relevant person who can then take appropriate therapeutic steps to attempt to address the increased fluid. In the present embodiment, if the impedance reaches a certain level or increases by a certain amount between two measurements, the CRT-D 44 can be programmed to increase the rate of support of the pulsatile device 42. More specifically, the CRT-D 44 can be programmed to increase the rate of support of the pulsatile device 42 so that it is inflating more often than prior to the increase in the fluid. In one example, the CRT-D 44 can increase the rate of support from 1:2 to 1:1. Alternatively, any desired increase can be implemented. In a further alternative, instead of the increasing the rate of support, the CRT-D 44 can be programmed to increase the amount that the pulsatile device 42 inflates.

In a further embodiment, the system 40 depicted in FIG. 2 can operate in a mode that can be called "internal cardiopulmonary resuscitation" (or "internal CPR"), in which the system 40 provides for complementary cardiac assistance in the event of an episode resulting in the loss of ventricular contraction or output (such as, for example, ventricular fibrillation, asystole, etc.) by providing a mechanical form of CPR or circulatory support via the pulsatile device 42 while concurrently providing a standard tiered electrical therapy via the electrical therapy device 44 (in this case, an CRT-D device 44). The CRT-D 44 can control the pulsatile device to pump the heart at a rate to maximize circulatory support until the electrical therapy is successful in restarting the heart or until emergency life support personnel arrive. The combined therapy will extend the capability of current life support devices, such as an ICD, in saving patients lives and provide greater cardiac resynchronization therapy for heart failure.

In operation of the internal CPR mode, the CRT-D 44 first detects a loss of ventricular contraction. At this point, the CRT-D 44 activates the pulsatile device 42 to begin providing "internal CPR" by issuing—via the lead 50—a pacing signal to the controller 46, which then actuates the pump in the controller 46 to pulsate the pulsatile device 42 via the drive line 48. More specifically, the loss of ventricular contraction means that there is no ventricular rhythm to sense and thereby actuate synchronized pacing using the electrical 44 and pulsatile devices 42. In response, the CRT-D 44 transmits instructions (in the form of a signal or signals) to the pulsatile device 42 (via the controller 46) to pulsate with a steady rate. The rate depends on, among other parameters, the type of assist device, the volume of displacement, and the slew rate for optimum cardiac output in the setting of no native ventricular contraction. According to one embodiment, a rate that produces a moderately rapid heartbeat of 80-120 BPM would provide an appropriate cardiac output. Alternatively, any rate that benefits the patient can be used.

In an alternative embodiment, instead of the CRT-D 44 issuing a signal to the controller 46 that the pulsatile device 42 should begin the internal CPR mode, the system can be operating in a synchronized pacing mode as described above and either the controller 46 or the pulsatile device 42 can sense that it is no longer receiving the standard pacing signal. As a result of this loss of signal, the controller 46 or the pulsatile device 42 can automatically actuate the device 42 to begin the internal CPR mode.

In a further embodiment, the CRT-D 44 can also transmit instructions to the pulsatile device 42 to pulsate with a specific inflation volume. The volume could be any volume that benefits the patient.

At the same time, the CRT-D 44 begins a known tiered electrical therapy process to attempt to return the heart to normal operation. In other words, while the CRT-D 44 is controlling the pulsatile device 42 to provide internal CPR in the form of mechanical pulsation assistance to the aorta, the CRT-D 44 is also applying tiered electrical therapy to attempt to return the heart to normal operation by first attempting to pace the heart back to normal operation, and then elevating the treatment ultimately to defibrillating the heart. It is understood that the pacing treatment can include burst pacing, anti-tachycardia pacing, or any pacing that may stimulate the heart back to normal operation. It is further understood that the defibrillation treatment includes a discharge defibrillation pulse. In one embodiment, the discharge pulse is typically applied between a superior vena cava lead (not shown) and the right ventricular lead (not shown) or in combination with discharge between the device 44 and defibrillation leads (not shown) positioned in the superior vena cava and the right ventricle. Alternatively, any known defibrillation treatment can be utilized.

In an alternative implementation, the CRT-D 44 first applies the known tiered therapy process as described above prior to activating the pulsatile device 42 to provide the "internal CPR" therapy. That is, instead of activating the "internal CPR" therapy as soon as the loss of ventricular contraction is detected, the CRT-D 44 first attempts to apply an electrical therapy (in the form of pacing and/or defibrillation).

Regardless of which therapy is applied first, the CRT-D 44 continues to operate the pulsatile device 42 to provide the internal CPR while also continuing to monitor the heart and provide the tiered electrical therapy (including defibrillation as necessary) until the heart returns to normal operation. Upon the heart returning to normal operation, the CRT-D 44 stops the internal CPR and returns the system to normal pacing—either standard electrical pacing or synchronized pacing combining electrical therapy and mechanical assistance with the pulsatile device 42.

Alternatively, the "internal CPR" mode can be implemented using impedance pump technology. Impedance pump technology, which is also referred to as "valveless pump" technology, relates to production of flow (including, for example, blood flow) along a length of tube having at least two sections, each of the sections having a different impedance. When the compliant portion of the tube is compressed, the resulting wave travels along the surface of the compliant portion and, when the wave reaches the interface with the portion having a different impedance, there will be at least a partial reflection of the wave. Repeated compressions along such a tube can which create a positive directional flow wave. This technology is described in further detail in Hickerson, Anna, "An Experimental Analysis of the Characteristic Behaviors of an Impedance Pump," California Institute of Technology, thesis (2005), and Schuit, E., "Valveless Impedance Pump Behavior, An Experimental Study," National University of Singapore and Eindhoven University of Technology, internship (2007), both of which are hereby incorporated herein by reference in their entireties.

For purposes of the internal CPR mode, the blood flow is created when the pulsatile device 42 provides mechanical pulsation assistance to the aorta, thereby causing the compliant aorta to oscillate and produce a standing wave of blood. As the blood flows into a non-compliant section of the aorta (such as, for example, the descending aorta of an elderly or diseased patient, which can be stiffer than a healthy aorta), positive blood flow can result. Depending on the amplitude and frequency of the displacements, clinically significant flow volumes can be attained. According to one embodiment, the driving rate can be 5-10 Hz (or 300 to 600 BPM). Alternatively, any known driving rate that can produce blood flow can be used. As such, according to one implementation, use of the pulsatile device 42 embodiments disclosed herein for purposes of an internal CPR mode can result in creation of positive blood flow in a situation in which the patient's heart is not beating. Alternatively, the impedance pump technology can also produce blood flow when operating asynchronously to the native heartbeat, thereby augmenting flow continuously above the natural heartbeat.

In another implementation, the system 40 depicted in FIG. 2 can operate in a mode that can be called the "internal workout" mode, in which the system 40 provides a heart strengthening treatment while also synchronously pacing the heart. More specifically, in this mode, the electrical device 44 and the pulsatile device 42 operate in synchronous fashion to intentionally create a stress or workload on the heart for a predetermined "workout" period. During the cardiac healing process, a weakened heart will become noticeably stronger with the assisted therapy being provided from an electrical therapy device and/or a pulsatile support device. It would be desirable to further aid recovery by providing an internal workout to the heart. The system 40 in this mode can potentially strengthen the heart to the point that the heart may not have to rely as much on the synchronized pacing treatment as it did prior to the heart strengthening treatment. Ultimately, the goal in any cardiac assistance support is to aid the patient to recovery or bridge the patient to transplant. If a patient is showing heart muscle recovery, the internal cardiac workout routine can be a method to ensure a complete and full recovery of cardiac function in a controlled and programmed manner. In one embodiment, the system 40 is operating in its synchronized pacing mode combined with a recurring heart strengthening treatment that repeats on a predetermined schedule. For example, in one embodiment, the heart strengthening treatment can be performed daily for an hour. Alternatively, the treatment can be performed on any predetermined schedule that is determined to benefit the patient.

In operation of the internal workout mode, according to one implementation, the system 40 is initially operating in its synchronized pacing mode. While operating in this mode, a workout mode can be implemented using resistance. More specifically, by controlling the timing between the electrical therapy device 44 and the pulsatile device 42, small amounts of resistance to contraction can be created. In one embodiment of the workout mode, either the CRT-D 44 or the controller 46 actuates the pulsatile device 42 to deflate later than in standard operation—after the left ventricle has begun to contract and urge blood into the aorta. The later deflation means that the aorta is still compressed for the period that the device 42 is still inflated, thereby providing resistance to the blood being urged into the aorta by the left ventricle. This resistance forces the left ventricle to contract with more strength in order to successfully urge the blood into the aorta. In other words, the left ventricle must "work harder" to get the same amount of blood into the aorta. As such, this resistance created by the later deflation of the pulsatile device 42 results in the heart having to work harder to operate. In another embodiment, instead of later deflation, the resistance is created by actuating the pulsatile device 42 to deflate to a partial volume (instead of fully deflating), resulting in aortic restriction during cardiac output that, like the later deflation, forces the left ventricle to "work harder."

In one implementation of the internal workout mode, the pulsatile device 42 deflates 25 mS later than during normal pacing. Alternatively, the device 42 deflates 50 mS later than normal. In a further embodiment, the device deflates by any amount ranging from about 10 mS to about 200 mS later than normal. In an alternative implementation in which the device 42 deflates to a partial volume, the device 42 deflates to 50% of its total volume for some predetermined period of time or number of heartbeats. Alternatively, the pulsatile device 42 can deflate by any amount ranging from about 10% to about 90% of its total volume for any predetermined period of time.

According to one embodiment of the internal workout mode, the device 42 operates in this mode for 30 minutes every 24 hours. Alternatively, the device 42 can operate in the internal workout mode for any desired amount of time and can be repeated on a cycle of any desired length. In addition, various embodiments of the internal workout mode can include increased resistance over time. For example, in one embodiment, the resistance might increase by some amount each cycle. In one exemplary embodiment, the deflation occurs 5% later in each cycle. Alternatively, the resistance can be increased every other cycle or on any other desired schedule.

In one implementation, the system 40 tracks the patient's response during the workout mode. More specifically, the CRT-D 44 senses heart characteristics, such as via the atrial lead and/or the right ventricular lead, during the workout mode. If the heart characteristics sensed by the device 44 indicate that the heart is being affected adversely by the resistance, the CRT-D 44 will stop the application of the resistance.

Figure 3A:
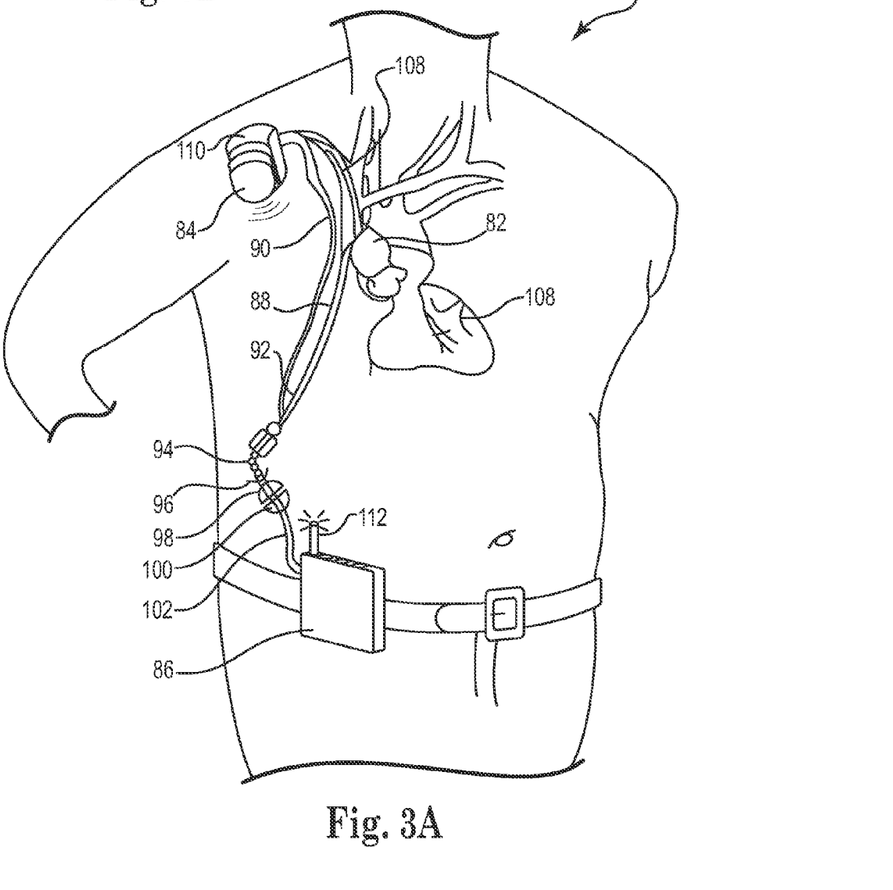
FIG. 3A is a cut away view of a patient with a combination heart assist system, in accordance with another embodiment.

In various alternative embodiments, systems having different configurations are contemplated that can perform all of the operational modes described above. For example, FIG. 3A depicts a system 80 having a pulsatile device 82 and an electrical therapy device 84. In one embodiment, the electrical therapy device 84 is a CRT-D 84 and the pulsatile device 82 is an aortic cuff 82. The pulsatile device 82 and the electrical device 84 are both coupled to an external driver/controller 86. More specifically, the pulsatile device 82 is coupled via a drive line 88 to a pump (not shown) in the driver/controller 86. The electrical device 84 is coupled to the driver/controller 86 via an electrical lead 90.

In the embodiment shown in FIG. 3A, the drive line 88 extends from the pulsatile device 82 to a "Y" connector 92. At the "Y" connector 92, the drive line 88 is positioned within an internal device coupling cable 94. The cable extends from the "Y" connector 92, through an incision 96 in the patient, and to a first connector 98 positioned outside the patient. The first connector 98 is removably coupled to a second connector 100 at one end of an external device coupling cable 102 that extends from the second connector 100 to the driver/controller 86. Thus, in this configuration, the drive line 88 extends from the pulsatile device 82, through the "Y" connector 92, through the incision 96, through the connection of first connector 98 and the second connector 100, and to the pump (not shown) in the driver/controller 86.

Figure 3B:
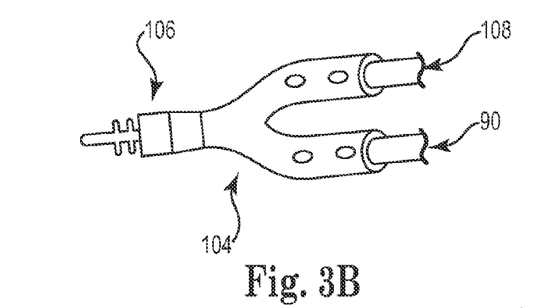
FIG. 3B is a front view of the "Y" connector incorporated into the combination heart assist system embodiment of FIG. 3A.

As best shown in FIGS. 3A and 3B, the electrical lead 90 extends from a "Y" connector 104 to the "Y" connector 92. The "Y" connector 104 is coupled to the electrical device 84 with an IS-1 connector 106. According to one embodiment, the "Y" connector 104 is any known "Y" connector such as the IS-1 Bif that is commercially available from St. Jude Medical in St. Paul, Minn. At the "Y" connector 92, the lead 90 is positioned within the internal device coupling cable 94. Thus, the lead 90 extends within the cable 94 through the incision 96, through the connection of the first and second connectors 98, 100 and to the driver/controller 86.

It should be noted that one difference between the system 40 depicted in FIGS. 2A and 2B and the system 80 depicted in FIGS. 3A and 3B is the "Y" connector 104 incorporated into the system 80 in FIGS. 3A and 3B. According to one embodiment, the "Y" connector 104 is included in the system 80 to allow for coupling the electrical device 84 to the controller 86 while also retaining the left ventricular lead 108. That is, in contrast to the system 40 in FIGS. 2A and 2B in which the left ventricular lead is removed from port 64C in the header block 64 so that it can be replaced with the connector lead 50, the "Y" connector 104 is used in the system 80 in FIGS. 3A and 3B to allow both the left ventricular lead 108 and the connector lead 90 to be coupled to the connector header 110. More specifically, the IS-1 connector 106 on the "Y" connector 104 can be inserted into a port in the connector header, and both the left ventricular lead 108 and the connector lead 90 can be coupled to the "Y" connector 104 as shown in FIGS. 3A and 3B and as discussed above, thereby making it possible for the connector lead 90 to be coupled to the device 84 without having to remove the left ventricular lead 108. In a further alternative embodiment, the header block can be a six-port header block as described above, which also allows both the left ventricular lead 108 and the connector lead 90 to be coupled to the header block. In one embodiment, a patient's response to CRT heart failure therapy can be relevant in determining whether to use an embodiment such as that set forth in FIGS. 2A and 2B (in which the connector lead 50 is coupled directly to the header block 64 and there is no left ventricular lead), an embodiment such as that set forth in FIGS. 3A and 3B (in which a bifurcated connection via a "Y" connector 104 provides for coupling both the connector lead 90 and the left ventricular lead 108 to the header block 110), an embodiment having a six-port header block, or some other embodiment. It is understood that the additional electrical sensing and pacing leads, such as, for example, the atrial and right ventricular leads (not shown), are also coupled to the header 110 in a fashion similar to that shown in FIGS. 2A and 2B. It is further understood that the distal ends of those leads are positioned in appropriate locations in the heart.

In a further alternative implementation, the "Y" connector 104 can be coupled to the connector lead 90 and to the right ventricular lead (not shown) (instead of the left ventricular lead 108).

In this embodiment, the controller 86 can communicate with the electrical therapy device 84 wirelessly. More specifically, the controller 86 has a wireless transceiver 112 that can transmit or receive wireless signals from the device 84. In one embodiment, the transceiver 112 is a radio frequency (RF) transceiver 112 that can transmit and receive RF signals. Alternatively, any known wireless technology can be used. According to one embodiment, the controller 86 and electrical device 84 can communicate with each other regarding the operational mode of the system. For example, in one embodiment, a user can enter information (such as by actuating a button or other actuation component) at the controller 86 about the desired mode. The controller 86 can then wirelessly transmit the information about the desired mode to the electrical device 84 via the wireless transceiver 112. In a further embodiment, during operation of one of the modes, the device 84 can transmit information about the operation of that mode (such as, for example, when the controller 86 should actuate the pulsatile device 82) to the controller 86. It is further understood that the communication capabilities of the system 80 can include any communication of any appropriate information between the two devices 84, 86 that can be helpful in operation of any of the modes described herein.

One exemplary CRT-D device 84 that can be incorporated into the system 80 and can communicate wirelessly with the controller 86 is Medtronic's Model D274TRK Concerto II CRT-D discussed above. The Concerto II CRT-D utilizes RF Conexus telemetry for wireless communication within the Medical Implant Communication Service (MICS) band. According to one implementation, this specific device 84 can use this RF Conexus telemetry functionality to communicate wirelessly with the controller 86 and exchange any information as described in any embodiment disclosed herein.

Figure 4:
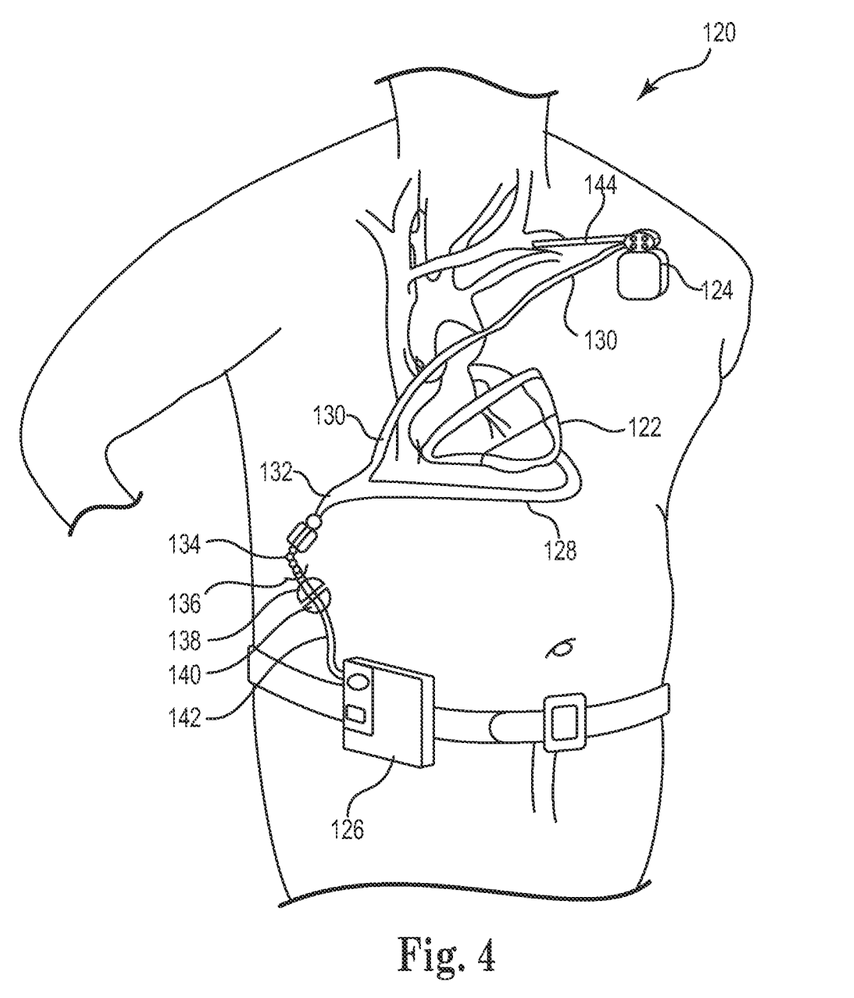
FIG. 4 is a cut away view of a patient with a combination heart assist system, according to another embodiment.

FIG. 4 depicts another embodiment of a system 120 having a ventricular pulsatile device 122, along with an electrical therapy device 124. In one embodiment, the electrical therapy device 124 is a CRT-D 124 and the ventricular pulsatile device 122 is positioned around the left ventricle. The pulsatile device 122 and the electrical device 124 are both coupled to an external driver/controller 126. More specifically, the pulsatile device 122 is coupled via a drive line 128 to a pump (not shown) in the driver/controller 126. The electrical device 124 is coupled to the driver/controller 126 via connector lead 130.

In the embodiment shown in FIG. 4, the drive line 128 extends from the pulsatile device 122 to a "Y" connector 132. At the "Y" connector 132, the drive line 128 is positioned within an internal device coupling cable 134. The cable extends from the "Y" connector 132, through an incision 136 in the patient, and to a first connector 138 positioned outside the patient. The first connector 138 is removably coupled to a second connector 140 at one end of an external device coupling cable 142 that extends from the second connector 140 to the driver/controller 126. Thus, in this configuration, the drive line 128 extends from the pulsatile device 122, through the "Y" connector 132, through the incision 136, through the connection of first connector 138 and the second connector 140, and to the pump (not shown) in the driver/controller 126.

Further, the electrical lead 130 extends from the electrical device 124 to the "Y" connector 132. At the "Y" connector 132, the lead 130 is positioned within the internal device coupling cable 134. Thus, the lead 130 extends within the cable 134 through the incision 136, through the connection of the first and second connectors 138, 140 and to the driver/controller 126.

In addition, the electrical sensing and pacing leads, including, for example, the right ventricular lead 144, are coupled to the electrical device 124. The distal ends of the leads are positioned in the appropriate locations in the heart.

In this embodiment, given that the pulsatile device 122 in this embodiment is a ventricular pulsatile device 122, it is understood that the timing of the actuation of the device 122 will be different than the aortic cuff embodiments discussed above. More specifically, the ventricular pulsatile device 122 is inflated to assist the left ventricle in contracting to force blood into the aorta (in contrast to the aortic cuff embodiments discussed above, which are actually deflated to assist the left ventricle in urging blood into the aorta).

In the implementation depicted in FIG. 4 (and in the other embodiments described herein and depicted in FIGS. 1-3B), the electrical therapy device 124 is coupled to the controller 126 via the connector lead 130. As described with respect to the various embodiments above, this direct coupling via the connector lead 130 allows the electrical device 124 and the controller 126 (and pulsatile device 122) to communicate. However, in certain alternative embodiments, no such direct coupling of the electrical device to the components of the pulsatile system is required. That is, the electrical device 124 and the controller 126 can communicate without a direct connection. In these embodiments, the electrical device 124 and controller 126 can communicate via wireless communication such as, for example, RF telemetry within the known Medical Implant Communication Service (MICS) band. Although the wireless communication in technology devices is generally not suited for real-time synchronous control due to processing delays and battery limitations, it is understood that future power sources and communication speeds may be suited for real-time control.

In further alternative embodiments relating to the systems contemplated herein (including those depicted in FIGS. 1-4), the controller is not a separate device. More specifically, in certain embodiments, the controller can be located in the electrical therapy device. In other embodiments, the controller can be located in the mechanical heart assist device.

Alternative combination system embodiments (having both an electrical therapy device and a mechanical heart assist device) can also include embodiments in which the electrical therapy device has no sensing lead. That is, in such implementations, instead of a sensing lead, the electrical therapy device has a sensor that can sense a heart characteristic without being positioned in or adjacent to the heart. For example, in one embodiment, the sensor is a sensing component that is not a lead and is configured to sense a heart characteristic. According to one implementation, the sensor is that is physically integrated into the electrical therapy device.

In further alternative implementations of combination systems, the electrical therapy device has no pacing lead. That is, in such implementations, instead of a pacing lead, the electrical therapy device has a pacing component that can stimulate or pace the heart without being positioned in or adjacent to the heart. In one example, the pacing component is a leadless cardiac stimulation component such as those disclosed in U.S. Published Application 2008/0109054 entitled "Leadless Cardiac Stimulation Systems," which is hereby incorporated herein by reference in its entirety.

Although the various embodiments disclosed herein have been described with reference to preferred embodiments, persons skilled in the art will recognize that changes may be made in form and detail without departing from the spirit and scope of the inventions.

What is claimed is:

1. A method of assisting and strengthening a heart, the method comprising:
   detecting a characteristic of a heart with a sensing lead;
   transmitting information about the heart characteristic to an electrical cardiac therapy device via the sensing lead;
   actuating the electrical cardiac therapy device based at least in part on the information about the heart characteristic;
   transmitting the information about the heart characteristic to a controller via a connecting lead coupled to the electrical cardiac therapy device and the controller;
   actuating an implantable mechanical heart assist device with an actuating signal from the controller, wherein the actuating is based at least in part on the information about the heart characteristic; and
   periodically timing the actuating of the mechanical heart assist device and the electrical cardiac therapy device such that a predetermined amount of resistance to contraction is created in the heart.

2. The method of claim 1, wherein the electrical cardiac therapy device is an ICD.

3. The method of claim 1, wherein the electrical cardiac therapy device is a CRT-D.

4. The method of claim 1, wherein the periodically timing the actuating of the mechanical heart assist device and the electrical cardiac therapy device further comprises timing the actuating of the devices such that the predetermined amount of resistance to contraction is created in the heart for a predetermined treatment period each day.

5. The method of claim 4, further comprising increasing or decreasing the predetermined treatment period as the heart is strengthened.

6. The method of claim 4, further comprising increasing or decreasing the predetermined treatment period after a predetermined amount of time.

7. The method of claim 1, wherein the controller is physically integral with the electrical cardiac therapy device.

8. The method of claim 1, wherein the controller is physically integral with the mechanical heart assist device.

9. The method of claim 1, wherein the mechanical heart assist device is a pulsatile device.

10. The method of claim 1, wherein the heart characteristic is chosen from the group consisting of heart vibrations, heart sounds, flow, pressure, impedance, wall stress, and optical reflectance.

11. The method of claim 1, further comprising periodically timing the actuating of the mechanical heart assist device and the electrical cardiac therapy device to operate synchronously to assist the heart based on the information about the heart characteristic.

12. The method of claim 1, wherein the periodically timing the actuating of the mechanical heart assist device and the electrical cardiac therapy device further comprises actuating the mechanical heart assist device to deflate after a left ventricle of the heart has begun to contract.

13. A method of assisting and strengthening a heart, the method comprising:
   detecting a characteristic of a heart with a sensor;
   transmitting a signal relating to the heart characteristic to an electrical therapy device via the sensor;
   actuating the electrical therapy device based at least in part on the heart characteristic signal;
   transmitting the heart characteristic signal from the electrical therapy device to a controller;
   actuating a mechanical heart assist device with an actuating signal from the controller, wherein the actuating is based at least in part on the heart characteristic signal; and
   periodically actuating the mechanical heart assist device to create a predetermined amount of resistance to contraction of the heart.

14. The method of claim 13, wherein the periodically actuating the mechanical heart assist device further comprises periodically timing the actuating of the mechanical heart assist device and the electrical therapy device.

15. The method of claim 14, wherein the periodically timing the actuating of the mechanical heart assist device and the electrical cardiac therapy device further comprises actuating the mechanical heart assist device to deflate after a left ventricle of the heart has begun to contract.

16. The method of claim 13, wherein the periodically actuating the mechanical heart assist device further comprises periodically actuating partial deflation of the mechanical heart assist device.

17. The method of claim 13, wherein the periodically actuating the mechanical heart assist device further comprises timing the actuating of the mechanical heart assist device such that the predetermined amount of resistance to contraction is created in the heart for a predetermined treatment period each day.

18. The method of claim 17, further comprising increasing or decreasing the predetermined treatment period as the heart is strengthened.

19. The method of claim 17, further comprising increasing or decreasing the predetermined treatment period after a predetermined amount of time.

20. A method of assisting and strengthening a heart, the method comprising:
- detecting a characteristic of a heart with a sensor;
- transmitting information about the heart characteristic to an electrical therapy device via the sensor;
- actuating the electrical therapy device based at least in part on the information about the heart characteristic;
- transmitting the information about the heart characteristic to a controller;
- actuating a mechanical heart assist device with an actuating signal from the controller, wherein the actuating is based at least in part on the information about the heart characteristic; and
- periodically actuating the mechanical heart assist device to create a predetermined amount of resistance to contraction of the heart.

21. The method of claim 20, wherein the periodically actuating the mechanical heart assist device further comprises periodically timing the actuating of the mechanical heart assist device and the electrical therapy device.

22. The method of claim 20, wherein the periodically actuating the mechanical heart assist device further comprises periodically actuating partial deflation of the mechanical heart assist device.

23. The method of claim 20, wherein the periodically actuating the mechanical heart assist device further comprises timing the actuating of the mechanical heart assist device such that the predetermined amount of resistance to contraction is created in the heart for a predetermined treatment period each day.

* * * * *